US005563282A

United States Patent [19]

McCain et al.

[11] Patent Number: 5,563,282
[45] Date of Patent: Oct. 8, 1996

[54] THERMAL PROCESS FOR REMOVAL OF CONTAMINANTS FROM PROCESS STREAMS

[75] Inventors: James H. McCain; Alfred W. Naumann; Wei-Yeong Wang, all of Charleston, W. Va.

[73] Assignee: Union Carbide Chemicals & Plastics Technology Corporation, Danbury, Conn.

[21] Appl. No.: 410,748

[22] Filed: Mar. 27, 1995

[51] Int. Cl.[6] .................... C07D 301/10; C07D 301/32; C07D 307/04
[52] U.S. Cl. .................................. 549/534; 549/538
[58] Field of Search .................... 549/538, 534

[56] References Cited

U.S. PATENT DOCUMENTS

| | | | |
|---|---|---|---|
| 1,403,160 | 1/1922 | Haner, Jr. . | |
| 1,483,160 | 2/1924 | Creighton . | |
| 1,522,091 | 1/1925 | Alexander . | |
| 2,238,007 | 4/1941 | Badenhausen | 23/48 |
| 2,673,787 | 3/1954 | Greenawalt | 23/48 |
| 2,690,425 | 9/1954 | Moses et al. | 210/2 |
| 2,691,569 | 10/1954 | Miller | 23/102 |
| 2,737,445 | 3/1956 | Nossen | 23/158 |
| 3,113,833 | 10/1963 | Bergstrom et al. | 23/48 |
| 3,333,917 | 2/1965 | Bergholm | 23/48 |
| 3,762,989 | 10/1973 | Timpe | 162/30 |
| 3,900,554 | 8/1975 | Lyon | 423/235 |
| 3,907,969 | 9/1975 | Field | 423/223 |
| 4,071,612 | 1/1978 | Weyer et al. | 423/659 |
| 4,100,263 | 7/1978 | Miller | 423/383 |
| 4,141,963 | 2/1979 | Miller | 423/592 |
| 4,206,186 | 6/1980 | Holter et al. | 423/230 |
| 4,208,245 | 6/1980 | Watkins et al. | 162/31 |
| 4,303,477 | 12/1981 | Schmidt et al. | 201/2.5 |
| 4,637,858 | 1/1987 | Matovich et al. | 162/30.1 |
| 4,981,659 | 1/1991 | Chuang et al. | 423/235 |
| 5,021,383 | 6/1991 | Berty | 502/174 |
| 5,059,405 | 10/1991 | Watson et al. | 423/210 |
| 5,114,692 | 5/1992 | Berty | 423/245.3 |
| 5,233,060 | 8/1993 | Pendergast et al. | 549/534 |
| 5,336,791 | 8/1994 | Jennings et al. | 549/534 |

FOREIGN PATENT DOCUMENTS

| | | |
|---|---|---|
| 53-19198 | 2/1978 | Japan . |
| 53-65262 | 6/1978 | Japan . |
| 56-54231 | 5/1981 | Japan . |
| 1415036 | 8/1973 | United Kingdom . |

OTHER PUBLICATIONS

"Screening Tests of Sodium Nitrite Decomposition", Kramer, et al., *Solar Energy Materials* 6 (1981) pp. 85–95.
"Preparation of Fine Oxide Powders by Evaporative Decomposition of Solutions", Roy, et al., *Ceramic Bulletin*, vol. 56, No. 11 (1977) pp. 1023–1024.
"A New High Temperature Aerosol Decomposition Process for the Synthesis of Mixed Metal Oxides for Ceramics and Catalysts and their Characterization", Moser, et al., *Chem. Eng. Comm.*, 1989, vol. X, pp. 1–19.
"A Novel Synthetic Method for the Preparation of Oxide Superconductors: Anionic Oxidation–Reduction", Kourtakis, et al., *Journal of Solid State Chemistry*, 82, pp. 290–297 (1989).
"Thermal Decomposition of Calcium Nitrate and Its Application in the Nitrogen Fertilizer Industry", Van Den Berg, et al., *Chemie–Ing.–Techn.*, 47 (20) pp. 845–846 (1975).

*Primary Examiner*—Joseph E. Evans
*Attorney, Agent, or Firm*—J. B. Mauro

[57] ABSTRACT

A method of controlling the build-up of organic and/or inorganic contaminants (e.g., carbonates, nitrates, nitrites, and the like) in an aqueous process stream, comprising directing at least some of the contaminated stream to a heating means wherein at least some of the contaminants are decomposed. Thereafter, the decomposition products are removed and the purified stream is returned to the process. In a preferred embodiment, the process is an alkylene oxide manufacturing process, and the contaminated aqueous stream is the effluent from a catalyzed scrubbing system for removal of carbon dioxide. Organic contaminants are decomposed to carbon dioxide, which is flashed off; inorganic salts which are decomposed to gases are flashed off; inorganic salts which are not converted to gases are scrubbed out.

15 Claims, 2 Drawing Sheets

THERMAL PROCESS FOR REMOVAL OF CONTAMINANTS FROM PROCESS STREAMS

BACKGROUND OF THE INVENTION

Commercial processes for manufacture of alkylene oxides, e.g., ethylene and propylene oxide, are well known. In a typical process, an alkylene is oxidized over a silver-containing catalyst to the corresponding oxide, which may be recovered or may be further reacted, e.g., with water to form the corresponding glycol. In such oxide manufacturing processes, carbon dioxide and various organic materials are often formed as unwanted by-products.

In a known process for removing the carbon dioxide, the carbon dioxide-bearing stream is scrubbed with an aqueous solution of alkali metal carbonates and/or bicarbonates. Such a process is described in, e.g., U.S. Pat. No. 3,907,969 and Great Britain Pat. No. 1,415,036, the disclosures of which are incorporated herein by reference. The process of that patent involves the use of vanadium and other catalytic materials which would be expensive to continually replenish, as well being undesirable to release to the environment. Accordingly, it is advantageous to provide an improvement to that process whereby the depleted scrubbing stream is treated to remove various contaminants, and is returned to the process.

A method for significantly improving the catalytic oxidation of the alkylene to the corresponding oxide has recently been disclosed in U.S. Pat. Appln. Ser. No. 091352, filed Jul. 14, 1993, the disclosure of which is incorporated herein by reference. This process utilizes silver catalysts of the type comprising at least one efficiency-enhancing salt of a member of a redox-half-reaction pair which are employed in processes in which at least one efficiency-enhancing gaseous member of a redox-half-reaction pair is present (described hereinbelow). When the process of this patent application is combined with the carbon dioxide removal process described above, undesirable nitrate and/or nitrite, as well as various organic, contaminants may be formed.

It has now been found that organic contaminants, as well as inorganic contaminants such as those resulting from processes such as those of the above-cited patent application, can be successfully removed, or optionally controlled in concentration, without significant destruction or depletion of the expensive chemicals required for the carbon dioxide scrubbing procedure, by the method reported below.

SUMMARY OF THE INVENTION

The present invention provides a method for controlling in a process the build-up of contaminants, typically organic contaminants, in an aqueous process stream bearing such contaminants, comprising:

(a) directing at least some of said aqueous process stream through a heating means under conditions sufficient to decompose at least part, and preferably all, of such contaminants, (b) directing the effluent from the heating means to at least one removal means for removing at least part of the decomposition products of the contaminants from said effluent, (c) optionally, dissolving in water at least part of said effluent after said removal of decomposition products, and (d) returning said contaminant-reduced effluent to said aqueous process stream.

Often, the method of this invention will be applied to a process stream which comprises a stream used for the removal of carbon dioxide from the process of which the process stream is a part. When so used, the contaminants likely will be contained in a process stream which contains alkali metal carbonates and/or bicarbonates.

In a preferred embodiment, the present invention provides a process for the manufacture of alkylene oxide comprising the catalytic oxidation of an alkylene, said process further comprising an aqueous recycle stream bearing dissolved contaminants comprising inorganic salts and organic materials, the improvement comprising:

(a) directing at least some of said recycle stream through a heating means under conditions sufficient to decompose at least part, and preferably all, of the organic materials and at least part of the inorganic salts, (b) removing the decomposition products of the organic materials and inorganic salts, (c) dissolving the remaining salts in water to form an aqueous solution, and (d) returning said aqueous solution to the alkylene oxide manufacturing process.

In a more specific preferred embodiment, the instant invention provides a process for the manufacture of alkylene oxide comprising the oxidation of an alkylene, said process further comprising an aqueous recycle stream containing dissolved alkali metal carbonate and/or bicarbonate salts from a $CO_2$ absorption step to a $CO_2$ desorption step and return, said stream further containing dissolved contaminants comprising organic impurities and/or nitrogen-containing salts, the improvement comprising controlling the build-up of contaminants by:

a) directing at least some of said recycle stream through a heating means under conditions sufficient to decompose at least part, and preferably all, of the organic materials and at least part of the inorganic salts, b) removing at least some, preferably all, products of the decomposition, c) dissolving remaining salts in water to form an aqueous solution, and d) returning said aqueous solution to the aqueous recycle of alkali metal carbonate/bicarbonate salts.

In another preferred embodiment, the instant invention provides a process for the manufacture of alkylene oxide comprising the oxidation of an alkylene, said process further comprising an aqueous recycle stream containing dissolved alkali metal carbonate and/or bicarbonate salts from a $CO_2$ absorption step to a $CO_2$ desorption step and return, said stream further containing dissolved contaminants comprising organic impurities and/or nitrogen-containing salts, the improvement comprising controlling the build-up of contaminants by:

a) directing at least some of said recycle stream through a heating means under conditions sufficient to take the salts to substantial dryness, b) heating the resulting dried salts under conditions sufficient to decompose at least part, preferably all, of the organic impurities and at least part, preferably all, of the nitrogen-containing salts, c) removing some, preferably all, products of the decomposition, d) dissolving remaining salts in water to form an aqueous solution, and e) returning said aqueous solution to the aqueous recycle of alkali metal carbonate/bicarbonate salts.

DESCRIPTION OF THE INVENTION

Figure 1:
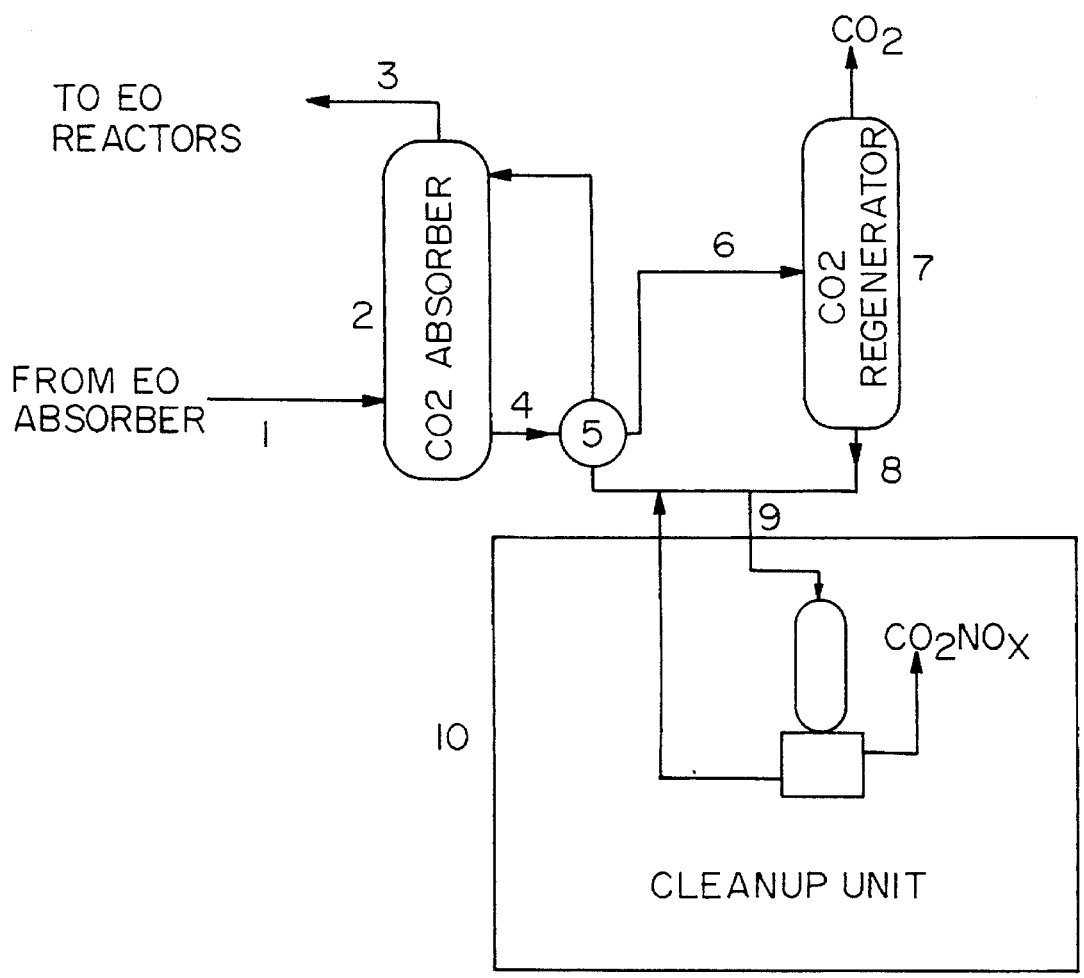
FIG. 1 is a flow diagram showing the general relationship of the present decontamination process to an alkylene oxide manufacturing process.

In its broadest embodiment, this invention contemplates the use of heat to decompose organic and/or inorganic materials which are present as contaminants, e.g., unwanted by-products, borne by an aqueous stream which forms part of a manufacturing process. Decomposition of the contaminants produces decomposition products, e.g., gases, which can be flashed off or stripped off by means well known in the art, thereby resulting in a purified or decontaminated stream which can be returned to the manufacturing process.

While it is expected that most contaminants will be dissolved in the aqueous stream, the invention is not intended to be limited to dissolved materials. For instance, organic contaminants could be borne is suspension or microemulsion form, and inorganic materials could be in insoluble, particulate form. By removal of at least some, and preferably all, of the contaminants by the thermal treatment of this invention, a purified aqueous stream can be returned to the manufacturing process, thereby controlling the buildup of the contaminants in the manufacturing process. It will be readily understood and appreciated that the present method is most conveniently applied to a manufacturing process through use of a recycle loop, i.e., the contaminated stream is channeled through the treatment method of this invention, and the decontaminated effluent of the present invention is returned to the manufacturing process. It will likewise be appreciated that the input to, and the output from, the present treatment method can be situated at any convenient point of the manufacturing process.

Processes where the method of this invention is particularly applicable include preparation of alkylene oxides, which can be recovered, or further processed to derivatives, such as glycols, alkanolamines, polyalkylene oxides and other polymers.

More specifically, one of the preferred embodiments of the invention relates to known processes for the catalytic conversion of ethylene to ethylene oxide, with subsequent hydrolysis of the ethylene oxide to ethylene glycol. Such a process is well known and is described in general terms in various publications (e.g., Kirk-Othmer *Encyclopedia of Chemical Technology,* 4th Ed., vol. 9, pages 915–960 (John Wiley & Sons, New York, 1994)), and in numerous U.S. and non-U.S. patents. Many variations on such a process, principally concerned with the catalysis aspects, are also disclosed in the art. See, for example, U.S. Pat. No. 5,187,140 and U.S. patent application Ser. No. 08/091,352, filed Jul. 14, 1993, the disclosures of which are incorporated herein by reference.

One particularly effective process for the preparation of ethylene oxide utilizes silver catalysts of the type comprising at least one efficiency-enhancing salt of a member of a redox-half-reaction pair which are employed in processes in which at least one efficiency-enhancing gaseous member of a redox-half-reaction pair is present (described hereinbelow). The term "redox-half-reaction" is defined herein to mean half-reactions like those found in equations presented in tables of standard reduction or oxidation potentials, also known as Standard or single electrode potentials, of the type found in, for instance, "*Handbook of Chemistry*", N. A. Lange, Editor, McGraw-Hill Book Company, Inc., pages 1213–1218 (1961) or "*CRC Handbook of Chemistry and Physics*", 65th Edition, CRC Press, Inc., Boca Raton, Fla., pages D155–162 (1984). The term "redox-half-reaction pair" refers to the pairs of atoms, molecules or ions or mixtures thereof which undergo oxidation or reduction in such half-reaction equations. Such terms as redox-half-reaction pairs are used herein to include those members of the class of substances which provide the desired performance enhancement, rather than a mechanism of the chemistry occurring. Preferably, such compounds, when associated with the catalyst as salts of members of a half-reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is a preferred cation, although sodium, rubidium and cesium may also be operable, and among the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The reaction conditions for carrying out the oxidation reaction are well known and extensively described in the prior art. This applies to reaction conditions, such as temperature, pressure, residence time, concentration of reactants, gas-phase diluents (e.g., nitrogen, methane and $CO_2$), gas-phase inhibitors (e.g., ethylene chloride and ethylene dichloride), and the like.

The gases fed to the reactor may contain modifiers or inhibitors or additives such as disclosed in U.S. Pat. Nos. 2,279,469 and 2,279,470, such as nitrogen oxides and nitrogen oxide-generating compounds.

The terms "gaseous member of a redox-half-reaction pair," "gaseous efficiency-enhancing member of a redox-half-reaction pair," or like terms referred to herein, have a meaning similar to that for the "salt of a member of a redox-half-reaction pair," or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing enhancing materials are compounds containing an element capable of existing in more than two valence states, preferably nitrogen and another element which is, preferably, oxygen. Examples of preferred gaseous efficiency-enhancing members of redox-half-reaction pairs include at least one of NO, $NO_2$, $N_2O_4$, $N_2O_3$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. NO is often preferred as the gaseous efficiency-enhancing compound.

The desirability of recycling unreacted feed, or employing a single-pass system, or using successive reactions to increase conversion by employing reactors in a series arrangement can be readily determined by those skilled in the art. The particular mode of operation selected will usually be dictated by process economics.

Generally, the commercially practiced processes for manufacturing ethylene oxide are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods.

As has been indicated, a typical process for the production of alkylene oxides produces significant amounts of carbon dioxide as a by-product. It is desirable to remove this material because concentrations of carbon dioxide much in excess of about 15 mole percent adversely affect the activity of the ethylene oxide catalyst. A preferred procedure for this removal is that described in U.S. Pat. No. 3,907,969, referred to above. This process for scrubbing carbon dioxide-containing aqueous streams, and the special chemical streams used for such scrubbing, are well known in the industry and are called the "Benfield process" and the "Benfield solution," respectively, owned and licensed by UOP, Inc., of Des Plaines, Ill. Accordingly, the present invention will be described, for convenience, principally with reference to the Benfield solution.

In a typical commercial design, the effluent stream from the carbon dioxide scrubbing column using the Benfield solution as the scrubbing agent goes largely (or completely depending where the removal unit takeoff stream is) to the $CO_2$ desorber. Economical and environmentally sound utilization of the Benfield process requires recycle of the effluent stream from the carbon dioxide desorbing column back to the carbon dioxide absorbing column. When contaminants build up in the Benfield solution to the point that the system no longer operates efficiently, the solution is taken in whole or in part to the decontamination unit, i.e., the unit which implements the method of this invention, where impurities as described previously are removed. From there, the solution is brought back to the Benfield scrubber and returned to the scrubber recycle stream. The organics present are primarily the acids formic and oxalic. It is important to remove such organics since they form acid salts with potassium and so tie up potassium that otherwise would be present as carbonate and available for removing carbon dioxide.

More specifically, referring to FIG. 1, $CO_2$-bearing gaseous stream 1 is fed to $CO_2$ absorber column 2 where it is contacted countercurrently with Benfield solution, i.e., an aqueous potassium carbonate/bicarbonate solution promoted with vanadium oxide and boric acid. Overhead stream 3, from which the $CO_2$ has been removed, is returned to the alkylene oxide manufacturing process. Bottoms stream 4 passes through heat exchanger 5 from which it is sent via stream 6 to a $CO_2$ regenerating column 7, in which $CO_2$ is separated and released to the atmosphere. Bottoms stream 8 from column 7 comprises an aqueous potassium carbonate/bicarbonate solution, promoted with vanadium oxide and boric acid, and contaminated with potassium organic acid salts, small amounts of alkylene glycol and, in the practice of certain embodiments of the method of U.S. patent application Ser. No. 091,352, mentioned above, also potassium nitrate/nitrite. Bottoms stream 8 is returned to the system until such time as the build-up of contaminants is found to be interfering with the efficient absorption of $CO_2$. At that time, slip stream 9 is diverted to contaminant removal (or "clean-up" unit) 10 for the practice of the present method. In general terms, the clean-up unit comprises heating means, separating means, and dissolution means, to perform the steps previously mentioned.

Figure 2:
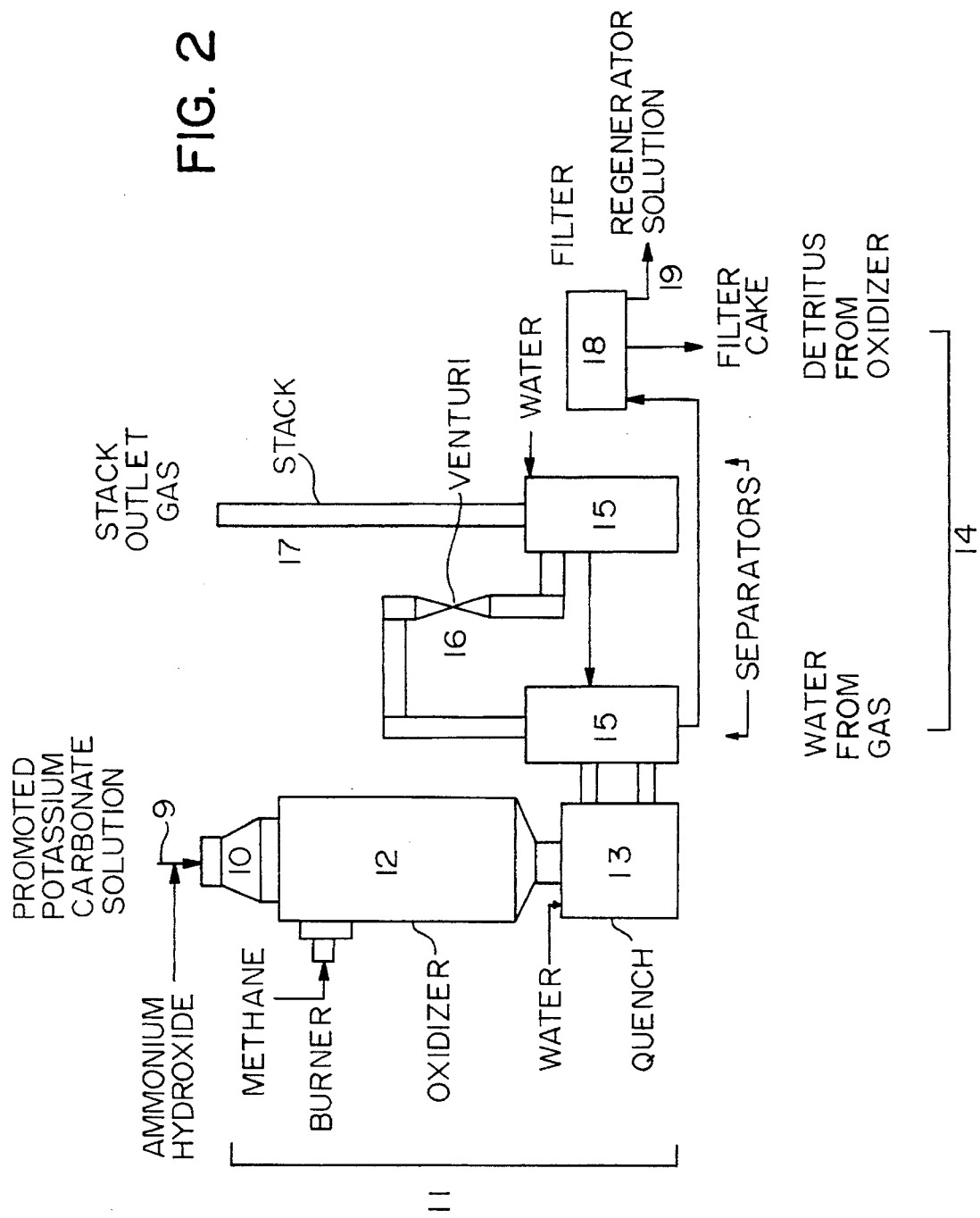
FIG. 2 is a flow diagram showing the use of a T-Thermal oxidizer, a preferred device for carrying out the decomposition and dissolution in the present process.

A preferred embodiment of clean-up unit 10 is depicted is FIG. 2, which relates to a T-Thermal SUB-X oxidizer (sold by T-Thermal, Inc., Conshohocken, Pa.) and associated equipment. To describe this device in general terms, the solution to be treated is sprayed into a high-temperature, flame-heated zone, water is evaporated, and the resulting particles of salt are pyrolyzed, all within a few seconds. A quench tank below the oxidizer scrubs the effluent gas to remove particulates, reconstituting the solution, now regenerated. Any molten salts hitting the wall run down with gravity into the quench. After the quench, the gas flows through a Venturi scrubber for final particulates removal and out through a stack. An advantage of the system is that solution is fed and solution is pumped out. No handling of solids nor operation of large pieces of rotating equipment is required. The system offers the added potential advantage that in situ NOx reduction may be practiced simply by adding ammonia to the feed; thus, regeneration and NOx reduction are combined in one operation.

Referring to FIG. 2, bottoms stream 9 from FIG. 1 is sprayed into radiant zone 10 of T-Thermal device 11, from which it passes into pyrolysis (oxidation) zone 12 for combustion with an appropriate fuel, such as natural gas. Ammonium hydroxide or ammonia may optionally be introduced into zone 10 to provide ammonia to assist in reduction of any $NO_x$ present. Introduction of ammonia or ammonium hydroxide is particularly advantageous to increase the decomposition of nitrites. In zone 12, the organic add salts will be converted to potassium carbonate and carbon dioxide, and glycol will be converted to carbon dioxide. Any potassium nitrite/nitrate will be regenerated to potassium carbonate and a gaseous nitrogen species. If ammonia (or ammonium hydroxide) has been introduced, the nitrogen species will be largely molecular nitrogen. If ammonium hydroxide (or ammonia) has not been introduced, the nitrogen species will be largely nitrogen oxides. The molten salts pyrolysis products run down the surface of oxidation zone 12 and pass into aqueous quench tank 13 where the regenerated salts are dissolved to form a solution which is routed to separation section 14, comprising aqueous scrubbers 15, Venturi scrubber 16, stack 17 to the atmosphere, and optionally filter 18 to remove any residual particulates. Separated gases, i.e., $CO_2$ and NOx (if produced) will be released through stack 17. Regenerated potassium carbonate solution 19 will be returned to the $CO_2$ absorption train.

Oxidation zone 12 is lined with refractory brick. It has been found that molten Benfield salts will react with and degrade some types of refractory brick, and will penetrate others. The best choice for refractory brick to resist degradation is believed to be a magnesium oxide brick known as "OXIBAK H," available from Harbison-Walker Refractories, Pittsburgh, Pa. However, since there is some penetration of OXIBAK H, it is considered useful to back it with a less penetrable brick such as "Greenal-90" from A. P. Green Industries, Inc. of Mexico, Mo.) Temperature in the oxidation zone should be kept reasonably constant, e.g., within about ±10° C., to minimize thermal cycling degradation of the refractory bricks.

While the present invention is described in relation to the Benfield process, it will be readily understood, however, that the procedures disclosed and claimed herein can also be effectively applied to processes other than the Benfield process, if appropriate.

In a preferred embodiment of the present invention, the method and materials of U.S. patent application Ser. No. 091352, mentioned above, are combined with those of the Benfield process. Under these conditions, it has been observed that a build-up of alkali nitrates and nitrites occurs in the Benfield solution, particularly when a nitrogen compound, e.g., an oxide of nitrogen, is used as a promoter for the ethylene oxide catalyst by conversion within the catalyst bed to nitrogen oxides. Such contamination should be removed because the nitrates, nitrites, and their inorganic acids reduce the effectiveness of the Benfield solution for carbon dioxide removal.

The percentage of the inorganic salts present which is decomposed is not critical; however, in order for the process to be operated under commercially efficient conditions of recycle, it is recommended that at least about 50 weight percent of the nitrates and at least about 50 weight percent of the nitrites be decomposed before return of the decontaminated recycle stream. It will be understood that the overall objective of the removal of the contaminants is to prevent their uncontrolled build-up in the process streams to concentrations which significantly interfere with the efficiency of the carbon dioxide absorption in the scrubbing column. It is recommended that the concentration of contaminants in continuous circulation be limited to no more than about 10%, based on the weight of the solution, preferably no more than about 5% nitrates, no more than about 10%, preferably no more than about 5% nitrites, and no more than about 10%, preferably no more than about 5% organics. Accordingly, the size of the stream sent to heat treatment should be determined so as to permit these steady-state concentration limits to be met after return of the decontaminated stream to the process.

Surprisingly, the decomposition temperatures of alkali metal nitrites and nitrates is not well known. For example, decomposition temperatures ranging from about 400° to about 1,000° C. have been reported for sodium and potassium nitrate (see C. M. Kramer, "Intrinsic Decomposition of Sodium Nitrate and Potassium Nitrate," Thesis, University of California, Davis, December 1980). While the operating temperature of the heating means is not narrowly critical, it has been found that for the streams being treated in the present invention, the heating means should be operated so as to subject the dry solids and organics to a temperature of at least about 300° C., and preferably at least about 350° C. Below about 300° C. the removal of contaminants begins to take an unacceptably long time. Upper temperature is determined primarily by equipment limitations and expense rather than reaction rates or products. An upper temperature due to equipment limitations might be in the range of about 1700° C. Preferred temperature is in the range of about 350° to about 1400° C.

In addition to the other inorganic salts, the stream will also contain a substantial concentration of carbonates, e.g., alkali carbonates, resulting from the reaction of the carbon dioxide with the Benfield solution. It is not critical to the method of this invention whether or not such carbonates are decomposed. If they are decomposed, they go to hydroxides or oxides, which are effective in $CO_2$ removal. If they are not decomposed, they stay as carbonates which also are effective in $CO_2$ removal.

While the preferred thermal treatment device is the T-Thermal oxidizer described above, the heating means can be any suitable device for applying the necessary heat while maintaining the materials in, handleable condition. For example, an oven or series of ovens could be employed, if appropriately designed to avoid melting of the salts. By way of guidance but not limitation, it has been found that simple pyrolysis in air at about 600° C. will remove essentially all nitrites and organics, but will provide little or no significant removal of nitrates. There may also be conversion of some nitrites to nitrates. The nitrates can be removed by treatment at about 750° C. or more; however, there is the likelihood of producing molten products which could be difficult to handle in an industrial facility.

A useful alternative to simple pyrolysis is the use of spray drying. Any of the numerous available spray drying devices should be satisfactory to take the contaminated Benfield solution to substantially dry powder. The powder can then be recovered and subjected to pyrolysis, as described above. Other alternative means of heat treatment include rotary calcination, band calcination and microwave treatment. Such methods, however, have the disadvantage of requiring either handling of solids, operation of large pieces of rotating equipment, or both. Care should also be taken to make sure the resulting solids are substantially dry, to avoid sticking or damming on the hot surfaces of the equipment. By "substantially dry" is meant the essential absence of a liquid phase.

It is considered to be desirable to conduct the heating in an inert, oxygen-lean atmosphere. Use of an inert atmosphere appears to reduce somewhat the temperatures needed to achieve decomposition. While any inert gas should be useful, the preferred gases are nitrogen and carbon dioxide. Complete absence of oxygen may, however, result in charring of organics; accordingly, an oxygen-lean environment is preferred to an oxygen-free one. The oxygen concentration should be maintained at a level of at least about 1% by volume to facilitate the decomposition of organics, and preferably in the range of about 3% to about 5%. Under these conditions, temperatures in the range of about 500°–600° C. should be satisfactory to accomplish the decomposition of the nitrogen-bearing salts and the organics.

EXAMPLES

Example 1

Into a four-foot diameter by eight-foot high refractory-lined chamber maintained at a temperature of 1880° F., an oxygen level of 5.0 vol. %, and a pressure of 5 psig with an internal gas-fired burner, was atomized at a rate of 90 pounds per hour an aqueous solution comprising a solution of potassium carbonate and potassium bicarbonate in water with proprietary promoters used for removal of carbon dioxide from an ethylene oxide process, 90 wt. %, ethylene glycol, 5 wt. %, potassium nitrate, 4.5 wt. %, and potassium nitrite, 0.5 wt. %. In use, the potassium carbonate/potassium bicarbonate solution had built up organic acid salts to an extent such that the feed solution contained about 10,500 parts per million by weight of formate ion and about 5,000 parts per million by weight of oxalate ion. From the chamber downstream of the injection point was pulled a sample of vapor and atomized salts, the salts having been in the heated chamber for a period of about 3.5 seconds. The salts were recovered by scrubbing in water, then the water was analyzed for nitrate, nitrite, formate, oxalate and potassium carbonate. Table 1 shows the results of analyses of the feed and of the water used to scrub the sample of vapor and salts. Adjusting the scrubber solution concentrations to the same carbonate level as the feed shows that formate and oxalate were completely decomposed, nitrate was 98+% decomposed, and nitrite was 42% decomposed. Nitrogen oxides were detected in the gaseous effluent from the unit in amount corresponding to 0.64 mole of nitrogen oxides per 1.00 mole of nitrite plus nitrate fed.

TABLE 1

|  | Carbonates, wt. % as $K_2CO_3$ | Nitrate, ppm[a] | Nitrite, ppm[a] | Formate, ppm[a] | Oxalate, ppm[a] |
| --- | --- | --- | --- | --- | --- |
| Feed Solution In | 33.02 | 28990 | 3495 | 10529 | 5350 |
| Scrubber Solution Out | 5.18 | 74 | 318 | 0 | 0 |

TABLE 1-continued

|  | Carbonates, wt. % as $K_2CO_3$ | Nitrate, ppm[a] | Nitrite, ppm[a] | Formate, ppm[a] | Oxalate, ppm[a] |
|---|---|---|---|---|---|
| Scrubber Solution Out adjusted to carbonates level of feed |  | 472 | 2027 | 0 | 0 |
| (% of feed concentration) |  | (1.6%) | (58%) | (0%) | (0%) |

[a] by weight

Example 2

This example shows the effect of ammonium hydroxide.

Into the chamber of Example I maintained at a temperature of 1880° F., an excess oxygen amount of 2.0 vol. %, and a pressure of 5 psig, was atomized the solution fed in Example 1, 132 pounds per hour, mixed with 25 wt. % aqueous ammonium hydroxide, 18.3 pounds per hour. The amount of ammonium hydroxide corresponded to 2.8 moles of ammonium hydroxide per 1.0 mole of nitrite plus nitrate. From the chamber downstream of the injection point was taken a sample of vapor and atomized salts, the salts having been in the heated chamber for a period of about 2.4 seconds. The salts were isolated by scrubbing in water, then the water was analyzed for nitrate, nitrite, formate, oxalate and potassium carbonate. Table 2 shows the results of analyses of the feed prior to mixing with ammonium hydroxide and of the water used to scrub the sample of vapor and salts. Adjusting the scrubber solution concentrations to the same carbonate level as the feed prior to mixing with ammonium hydroxide shows that formate and oxalate were completely decomposed, nitrate was 99+% decomposed, and nitrite was 95+% decomposed. Nitrogen oxides were detected in the gaseous effluent from the unit in amount corresponding to 0.16 mole of nitrogen oxides per 1.00 mole of nitrite plus nitrate fed. Under the same conditions without ammonium hydroxide, nitrogen oxides were detected in the effluent in amount of 0.66 mole of nitrogen oxides per 1.00 mole of nitrite plus nitrate fed. Thus nitrogen oxides were reduced by 76% when ammonium hydroxide was fed. Also, the conversion of nitrite was increased from 42% (Example 1) to 95+% when ammonium hydroxide was fed.

Into the chamber of Example 1 maintained at a temperature of 2000° F., an excess oxygen level of 1.2 vol. %, and a pressure of 5 psig, was sprayed the solution fed in Example 1, 90 pounds per hour, mixed with 25 wt. % aqueous ammonium hydroxide, 8.5 pounds per hour. The amount of ammonium hydroxide corresponded to 1.6 moles of ammonium hydroxide per 1.0 mole of nitrite plus nitrate. From the chamber downstream of the injection point was taken a sample of vapor and atomized salts, the salts having been in the heated chamber for a period of about 2.4 seconds. The salts were isolated by scrubbing in water, then the water was analyzed for nitrate, nitrite, formate, oxalate and potassium carbonate. Table 3 shows the results of analysis of the feed prior to mixing with ammonium hydroxide and of the water used to scrub the sample of vapor and salts. Adjusting the scrubber solution concentrations to the same carbonate level as the feed prior to mixing with ammonium hydroxide shows that formate and oxalate were completely decomposed, nitrate was 99+% decomposed, and nitrite was 90% decomposed. Nitrogen oxides were detected in the gaseous effluent from the unit in amount corresponding to 0.55 mole of nitrogen oxides per 1.00 mole of nitrite plus nitrate fed. Under the same conditions without ammonium hydroxide added to the feed, nitrogen oxides were detected in the effluent in amount of 0.78 mole of nitrogen oxides per 1.00 mole of nitrite plus nitrate fed. Thus, nitrogen oxides were reduced by 29% when ammonium hydroxide was fed at the level indicated.

TABLE 2

|  | Carbonates, wt. % as $K_2CO_3$ | Nitrate, ppm[a] | Nitrite, ppm[a] | Formate, ppm[a] | Oxalate, ppm[a] |
|---|---|---|---|---|---|
| Feed Solution In | 33.02 | 28990 | 3495 | 10529 | 5350 |
| Scrubber Solution Out | 1.95 | 4 | 9 | 0 | 0 |
| Scrubber Solution Out adjusted to carbonates level of feed |  | 68 | 152 | 0 | 0 |
| (% of feed concentration) |  | (0.2%) | (4%) | (0%) | (0%) |

[a] by weight

Example 3

This example shows the effect of a lower amount of ammonium hydroxide and higher temperature.

TABLE 3

|  | Carbonates, wt. % as $K_2CO_3$ | Nitrate, ppm[a] | Nitrite, ppm[a] | Formate, ppm[a] | Oxalate, ppm[a] |
|---|---|---|---|---|---|
| Feed Solution In | 33.02 | 28990 | 3495 | 10529 | 5350 |
| Scrubber Solution Out | 2.98 | 4 | 31 | 0 | 0 |
| Scrubber Solution Out |  | 44 | 343 | 0 | 0 |

TABLE 3-continued

| | Carbonates, wt. % as $K_2CO_3$ | Nitrate, ppm[a] | Nitrite, ppm[a] | Formate, ppm[a] | Oxalate, ppm[a] |
|---|---|---|---|---|---|
| adjusted to carbonates level of feed | | | | | |
| (% of feed concentration) | | (0.2%) | (10%) | (0%) | (0%) |

[a]by weight

Example 4

This example shows the effect of ammonia and higher pressure.

Into the chamber of Example 1 maintained at a temperature of 1930° F., an excess oxygen amount of 1.2 vol. %, and a pressure of 11 psig, was sprayed the solution fed in Example 1, 90 pounds per hour, mixed with 100 wt. % ammonia, 1.16 pounds per hour. The amount of ammonia corresponded to 1.7 moles of ammonium hydroxide per 1.0 mole of nitrite plus nitrate. From the chamber downstream of the injection point was taken a sample of vapor and atomized salts, the salts having been in the heated chamber for a period of about 3.5 seconds. The salts were isolated by scrubbing in water, then the water was analyzed for nitrate, nitrite, formate, oxalate and potassium carbonate. Table 4 shows the results of analysis of the feed prior to mixing with ammonia and of the water used to scrub the sample of vapor and salts. Adjusting the scrubber solution concentrations to the same carbonate level as the feed prior to mixing with ammonium hydroxide shows that formate and oxalate were completely decomposed, nitrate was 99+% decomposed, and nitrite was 90% decomposed. Nitrogen oxides were detected in the gaseous effluent from the unit in amount corresponding to 0.24 mole of nitrogen oxides per 1.00 mole of nitrite plus nitrate fed. Under the same conditions without ammonia added to the feed, nitrogen oxides were detected in the effluent in amount of 0.86 mole of nitrogen oxides per 1.00 mole of nitrite plus nitrate fed. Thus, nitrogen oxides were reduced by 72% when ammonia was fed.

ion. Nitrite decomposition was 96%, nitrate decomposition was 53%, oxalate and formate decompositions were 100%.

We claim:

1. A method for controlling in a process the build-up of contaminants in an aqueous process stream bearing such contaminants, said aqueous process stream comprising an aqueous recycle stream containing dissolved alkali metal carbonate and/or bicarbonate salts from a $CO_2$ absorption step to a $CO_2$ desorption step and return, said process comprising:

(a) directing at least some of said aqueous process stream through a heating means under conditions sufficient to decompose at least part of such contaminants, (b) directing the effluent from the heating means to at least one removal means for removing at least part of the decomposition products of the contaminants from said effluent, (c) optionally, dissolving in water at least part of said effluent after said removal of decomposition products, and (d) returning said contaminant-reduced effluent to said process.

2. A method of claim 1 wherein said aqueous process stream is a recycle stream.

3. A method of claim 1 wherein said contaminants comprise organic materials and inorganic materials.

4. A process for the manufacture of alkylene oxide comprising the oxidation of an alkylene, said process further comprising the use of an aqueous recycle stream containing

TABLE 4

| | Carbonates, wt. % as $K_2CO_3$ | Nitrate, ppm[a] | Nitrite, ppm[a] | Formate, ppm[a] | Oxalate, ppm[a] |
|---|---|---|---|---|---|
| Feed Solution In | 33.02 | 28990 | 3495 | 10529 | 5350 |
| Scrubber Solution Out | 3.09 | 5 | 33 | 0 | 0 |
| Scrubber Solution Out adjusted to carbonates level of feed | | 53 | 352 | 0 | 0 |
| (% of feed concentration) | | (0.2%) | (10%) | (0%) | (0%) |

[a]by weight

Example 5

Into a 6.5-inch diameter by 11.5-foot long rotary calciner heated at 620° C. were fed over 52 minutes approximately 13 pounds of dried salts from Benfield solution. The salts contained 3.10 wt. % nitrate ion, 3.35 wt. % nitrite ion, 1.94 wt. % oxalate ion, and 5.15 wt. % carbonate ion. Salt residence time within the calciner was approximately one-half hour. Nitrogen at 3 cu. ft. per min. was fed countercurrently relative to salts through the calciner. The oxygen level in the gas exiting the calciner was 9 volume percent. Calcined product, 8.1 pounds, was obtained, which contained from grab sample analysis 0.12 wt. % nitrite ion, 1.57 wt. % nitrate ion, 0.00% oxalate ion, and 0.00 wt. % formate dissolved alkali metal carbonate and/or bicarbonate salts from a $CO_2$ absorption step to a $CO_2$ desorption step and return, said stream further containing dissolved contaminants comprising organic impurities and/or nitrogen-containing salts, the improvement comprising controlling the build-up of contaminants by:

a) directing at least some of said recycle stream through a heating means under conditions sufficient to decompose at least part of the organic materials and at least part of the inorganic salts, b) removing gaseous products of the decomposition, c) dissolving remaining salts in water to form an aqueous solution, and d) returning said aqueous solution to the aqueous recycle of alkali metal carbonate/bicarbonate salts.

5. A process of claim 4 wherein the heating is done in an oxygen-lean atmosphere.

6. A process of claim 4 wherein the heating is done at a temperature above about 300° C.

7. A process of claim 6 wherein the inorganic salts comprise oxides of nitrogen.

8. A process for the manufacture of alkylene oxide comprising the oxidation of an alkylene, said process further comprising the use of an aqueous recycle stream containing dissolved alkali metal carbonate and/or bicarbonate salts from a $CO_2$ absorption step to a $CO_2$ desorption step and return, said stream further containing dissolved contaminants comprising organic impurities and/or nitrogen-containing salts, the improvement comprising controlling the build-up of contaminants by:

a) directing at least some of said recycle stream through a heating means under conditions sufficient to take the salts to substantial dryness, b) heating the resulting dried salts under conditions sufficient to decompose at least part of the organic impurities and at least part of the nitrogen-containing salts, c) removing gaseous products of the decomposition, d) dissolving remaining salts in water to form an aqueous solution, and e) returning said aqueous solution to the aqueous recycle of alkali metal carbonate/bicarbonate salts.

9. A process of claim 8 wherein the heating is done in an oxygen-lean atmosphere.

10. A process of claim 8 wherein the heating is done at a temperature above about 300° C.

11. A process of claim 10 wherein the inorganic salts comprise oxides of nitrogen.

12. A process of claim 4 in which step (a) further comprises introducing ammonia or ammonium hydroxide into the heating means.

13. A process of claim 8 in which step (a) further comprises introducing ammonia or ammonium hydroxide into the heating means.

14. A method of claim 1 wherein said contaminants are contained in a process stream which contains alkali metal carbonates or bicarbonates.

15. A method of claim 1 wherein the heating is done in an oxygen-lean atmosphere.

\* \* \* \* \*